United States Patent [19]
Legrand

[11] Patent Number: 5,921,988
[45] Date of Patent: Jul. 13, 1999

[54] INSTALLATION INSTRUMENT FOR A BLADE SUTURE CLIP FOR OSTELOGICAL REMOVAL FOR THE TREATMENT OF INFLAMMATION OF THE KNEE JOINT

[75] Inventor: Jean-Jacques Legrand, Chambery, France

[73] Assignee: Proseal, France

[21] Appl. No.: 08/967,576

[22] Filed: Nov. 10, 1997

[30] Foreign Application Priority Data

Nov. 8, 1996 [FR] France .................................... 96 13840

[51] Int. Cl.$^6$ ........................................................ A61F 5/04
[52] U.S. Cl. ................................................................ 606/87
[58] Field of Search .............................. 606/232, 72, 74, 606/76, 75, 79, 84, 86, 87, 88, 89, 96

[56] References Cited

U.S. PATENT DOCUMENTS

| | | | |
|---|---|---|---|
| 5,053,039 | 10/1991 | Hofmann et al. | 606/87 |
| 5,246,444 | 9/1993 | Schreiber | 606/87 |
| 5,720,752 | 2/1998 | Elliot et al. | 606/88 |

FOREIGN PATENT DOCUMENTS

WO 94/02073  2/1994  WIPO.
WO 96/24295  8/1996  WIPO.

OTHER PUBLICATIONS

French Search Report dated Jul. 21, 1997 corresponding to priority document application number 96/13840.

*Primary Examiner*—Michael Buiz
*Assistant Examiner*—Vikki Trinh
*Attorney, Agent, or Firm*—Young & Basile, P.C.

[57] ABSTRACT

Installation for a blade suture clip for osteological removal for treatment of the inflammation of the knee joint. The instrument consists of a positioning-reduction frame presenting an opening meant to position a piercing block in order to create holes allowing the installation of the blade suture clip. The opening is limited by two proximal edges and two distal edges, and two lateral edges presenting an extension similar to that of the blade suture clip. The proximal part of each of the lateral edges contains superimposed holes to position the positioning reduction frame by means of pins, while the distal edge contains a hole designed for the passage of the proximal bit of a tightening instrument allowing adjustment of compression while the distal bit is introduced in a hole pierced in the tibia under the distal edge of the positioning-reduction frame at a certain distance.

10 Claims, 3 Drawing Sheets

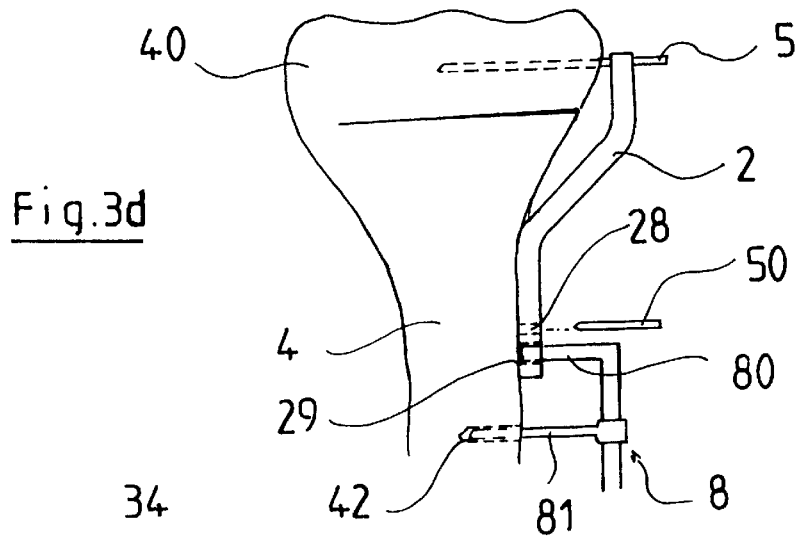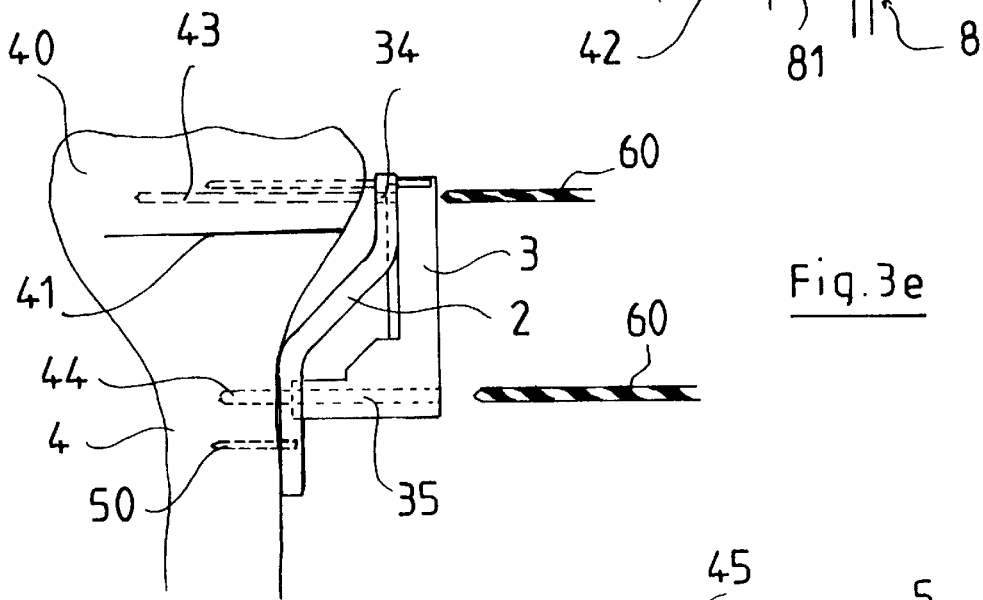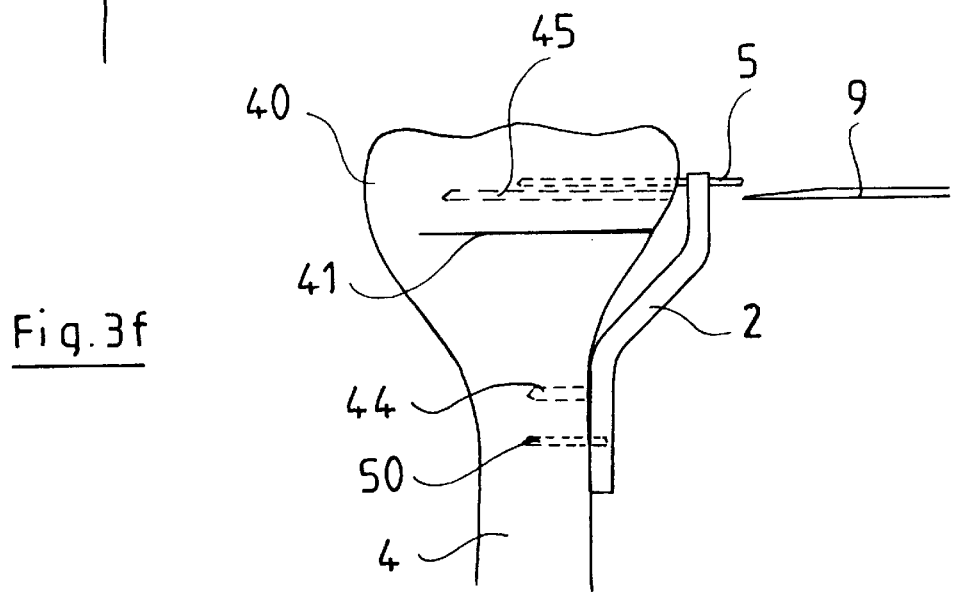

5,921,988

INSTALLATION INSTRUMENT FOR A BLADE SUTURE CLIP FOR OSTELOGICAL REMOVAL FOR THE TREATMENT OF INFLAMMATION OF THE KNEE JOINT

BACKGROUND OF THE INVENTION

The present invention is an installation instrument for a blade suture clip for osteological removal for the treatment of inflammation of the knee joint.

Osteological removal is an operation technique which consists of correcting a deformation of the knee bent inward at the tibia and, more rarely bent outward at the femur.

This operational technique, for the treatment of a bent inward knee, for example, consists of achieving a partial osteotomy from the external side in the upper epiphysis of the tibia, that is to say, by keeping the joint on the internal side, and maintaining this angular correction until the osteogenesis.

The difficulty of this treatment rests in maintaining the degree of correction post-operatively as it was before the operation.

In order to maintain this degree of correction, one uses an implant which can be a screw-plate, or a swan-collar blade plate, or a suture grip plate, for example.

These different implants give total satisfaction regarding the result, while they present the inconveniences of requiring a rather long operating time, especially to put in place the screw-plate or the blade plate, and a large access or skin incision.

SUMMARY OF THE INVENTION

The goal of the present invention is to propose an instrument for installing a blade suture clip allowing reduction in operating time and to facilitate the installation.

A blade suture clip consists of a suture clip designed to be positioned spanning the osteotomy after reducing the focus/center of the osteotomy.

The blade suture clip consists of a proximal blade designed to be impacted in a fissure pierced crosswise in the epiphysis above the osteotomy, and two distal teeth designed to be impacted in the holes pierced under the osteotomy, the blade and the teeth being brought together by an intermediary part allowing an indentation in order to create a gap, the amplitude of which is a function of the morphology of the tibia.

The installation of a blade suture clip according to the invention is characterized by containing a positioning-reduction frame presenting an opening designed to position a piercing block in order to reach the holes allowing the installation of the blade suture clip, the opening being marked by proximal and distal edges, and two lateral edges showing an indentation similar to that of the blade suture clip, that is to say, the proximal and distal parts of the frame are roughly parallel but in different planes spaced at a length corresponding to the amplitude of the gap from the blade suture clip. The proximal part of each of the lateral edges contains superimposed holes meant to position the frame by means of pins, while the distal edge contains a hole designed for the passage of the proximal bit of a tightening instrument allowing one to maintain the compression while the distal bit is introduced into a hole pierced in the tibia under the frame at a certain distance from the distal edge of the frame.

According to an additional characteristic of the instrument of the invention, the passing hole for the joint of the tightening instrument is oblong in a vertical direction.

According to another characteristic of the invention, the distal edge of the positioning-reduction frame contains a second hole, situated below the first hole, and meant to receive a pin allowing the independent compression of the tightening instrument.

In accordance with the invention, the piercing block contains at its proximal end a series of juxtaposed holes pierced in the frontal direction and designed to allow piercing into the bone holes to prepare the slit to lodge the blade of the blade suture clip; and at its distal end, two holes arranged next to each other, pierced on the frontal direction with the space between the two holes corresponding to those of the teeth of the blade suture clip, and designed to lodge in the teeth.

Still in accordance with the invention, a piercing template, designed to be adapted into the positioning-reduction frame, contains a distal extension which cuts off the distal edge of the positioning-reduction frame, and which is pierced in the front by a hole allowing the piercing into the bone of the hole for introduction of the distal bit of the tightening instrument.

According to another embodiment; the piercing template makes up an integral part of the piercing block and consists of a distal extension of the piercing block.

BRIEF DESCRIPTION OF THE DRAWING

The advantages and characteristics of this invention will become more clear in the description which follows and related to the attached drawing, which is pictured in non-limiting manner.

In the attached drawing:

FIGS. 3a, 3b, 3c, 3d, 3e and 3f represent schematic views of different phases of the preparation of the installation of a blade suture clip by means of an instrument according to the invention.

DESCRIPTION OF THE PREFERRED EMBODIMENT

Figure 1:
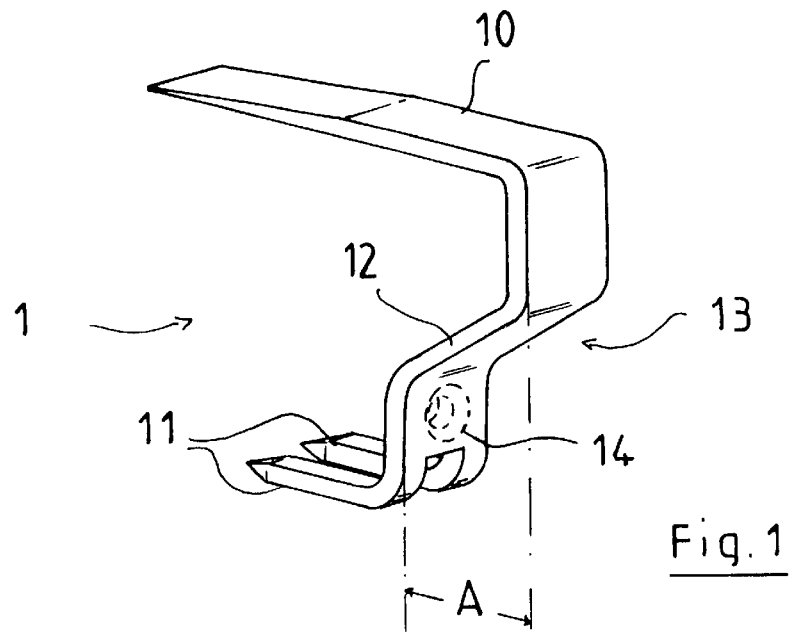
FIG. 1 represents a perspective view of a blade suture clip according to the invention.

If one refers to FIG. 1, one can see that a blade suture clip 1 containing a proximal blade 10 linked to two distal teeth 11 by an intermediate part 12 having an indentation 13 of a certain amplitude A, which allows the approximate following of the epiphysis and upper metaphysis of the external face of a tibia. The amplitude A is variable by the function of the anatomy, which is determined before operating.

Figure 2:
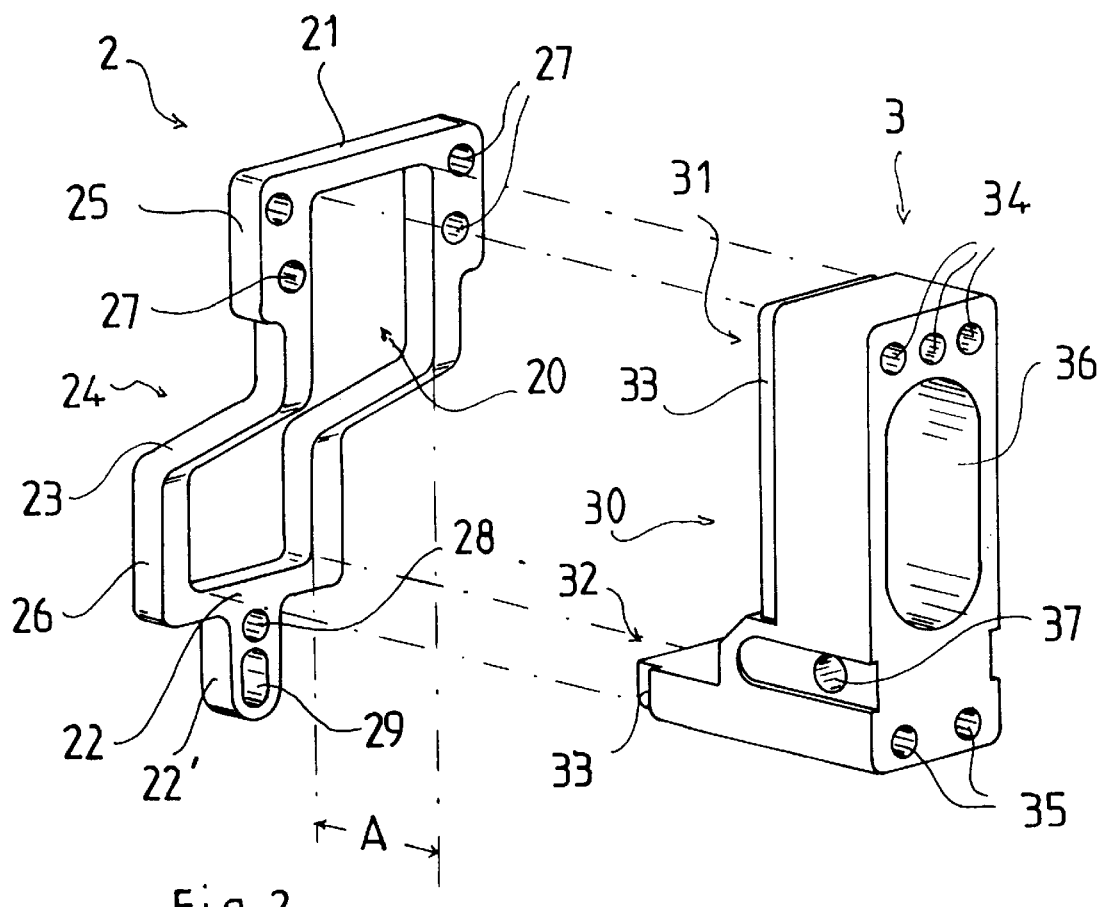
FIG. 2 represents a perspective exploded view of an installing instrument for a blade suture clip according to the invention.

If one now refers to FIG. 2, one can see a blade suture clip installation instrument according to the invention which contains a positioning-reduction frame 2 and a piercing block 3, The positioning-reduction frame 2 consists of a central opening 20 defined by a proximal edge 21, a distal edge 22, and two lateral edges 23 showing an indentation 24 corresponding to the amplitude A of the blade suture clip 1 such that proximal parts 25 and distal parts 26 are in different parallel planes.

The proximal part 25 of the lateral edges 23 are pierced in the frontal direction by superimposed holes 27, while the distal edge 22 contains in its middle region an extension 22' jutting out towards the bottom and pierced roughly parallel to the holes 27 by two superimposed holes 28 and 29, the lowest hole being oblong.

The piercing block 3 contains a coupling face 30 opposed to the positioning-reduction frame 2 and having two parts: a distal coupling part 32 opposed to the distal edge 22 and the distal part 26 of the lateral edges 23, and a proximal part 31 coupling to the proximal edge 21 and the proximal part 25 of the lateral edges 23, the coupling being achieved by the intermediary of a peripheral shouldering wall 33.

The piercing block 3 contains near its proximal end three juxtaposed frontal holes 34, and near its distal end two frontal holes 35, placed next to each other and superimposed corresponding to the teeth 11 of the blade suture clip 1, while a aperture 36 is located centrally between the holes 34 and 35 allowing visual access to the opening 20 of the positioning reduction frame 2.

One will note that the piercing block 3 contains a hole 37 located crosswise in its distal part and designed to be adapted to a maintenance handle, not shown.

The preparation to put in place the blade suture clip 1 by means of an instrument according to the invention will now be described and illustrated by FIGS. 3a, 3b, 3c, 3d, 3e, and 3f, where an upper epiphysis 40 of a tibia 4 is represented.

Figure 3A:
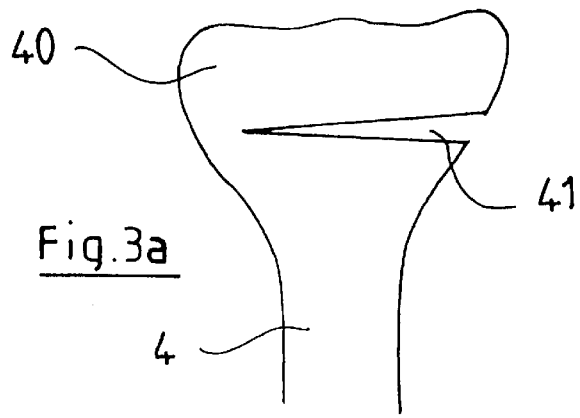

In FIG. 3a, one pierces an osteotomy 41 in the epiphysis 40 its site determined by placing the positioning-reduction frame 2 there, not represented, corresponding to the blade suture clip to be implanted, the amplitude of the clip 1 corresponding to the morphology of the tibia 4.

Figure 3B:
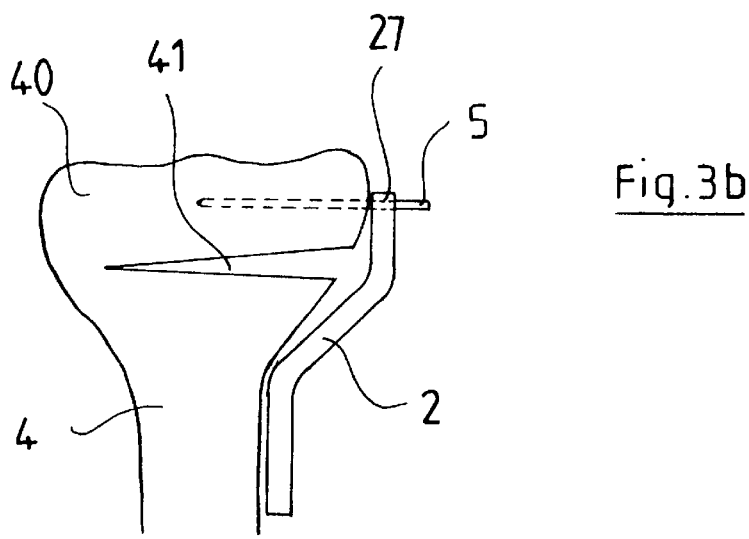

In FIG. 3b, the positioning-reduction frame 2 is placed on the epiphysis 40 and is fixed in position by means of at least two, and preferably four headless pins 5 introduced in the proximal holes 27 of the positioning-reduction frame 2.

Figure 3C:
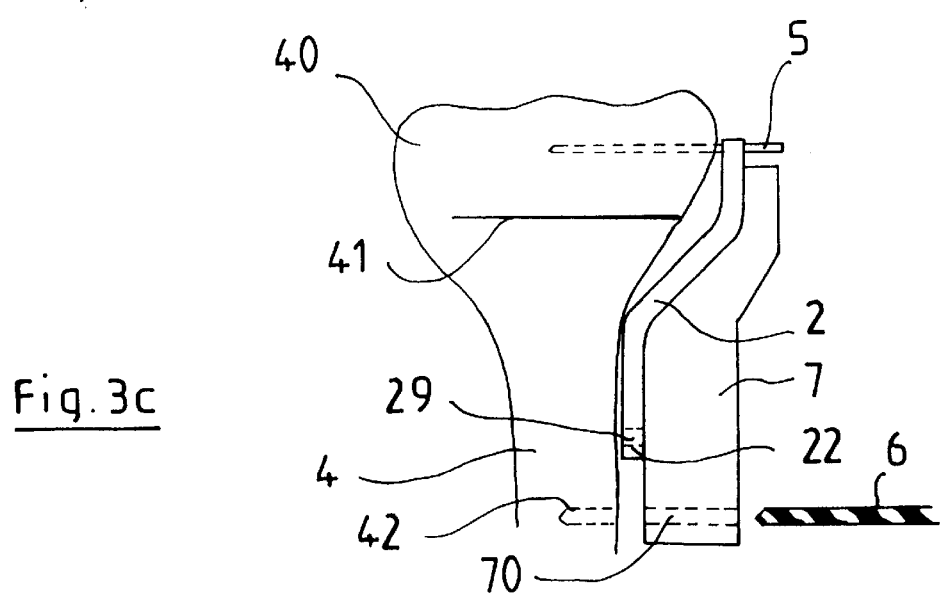

In FIG. 3c, the focus of the osteotomy 41 is reduced, which is achieved manually in order to allow the piercing of a hole 42 in the tibia 4 under the distal edge 22 of the frame 2 by means of a packing 6 introduced in the distal hole 70 of a template 7 secured to the frame 2.

One will note that according to a variance, not represented, the template 1 can consist of a block containing a distal hole and a proximal hook designed to hang in the distal hole 29, of which the lower edge is preferably indented into the side of the tibia 4 in order to allow a good hanging.

According to another variant, not represented, the piercing block 3 contains a distal extension pierced by a hole allowing the piercing of the hole 42.

In FIG. 3d, the reduction of the focus of the osteotomy 41 is maintained, without being increased, by means of a clamp 8 of which a proximal bit 80 is introduced in the hole 42 pierced in the tibia 4. After the complete reduction of the focus of osteotomy 41, a pin 50 can be introduced into the hole 28 of the frame 2 in order to fix the frame 2 in position.

It is also possible to pierce the hole 42 before the reduction of the osteotomy, which can be achieved only by means of the clamp 8.

The clamp 8 must therefore be of a well-designed, which explains the oblong shape of the hole 29 of the frame 2, in order to allow the passage of the proximal bit 80 through the hole 29 in the frame 2.

In FIG. 3e, the piercing block 3 is adapted onto the positioning-reduction frame 2, and three proximal holes 43, of which only one is visible in the drawing, and two distal holes 44, of which only one is visible in the drawing, are pierced in the epiphysis 40 by means of a packing 60 introduced in the holes 34 and 35 of the piercing block 3.

One will note that these piercing operations can be achieved while the frame 2 is held by the clamp 8, not shown.

Finally, in FIG. 3f, the piercing block 3 is raised, and a slit 45 is made by means of shaped scissors 9 which cut the bone material separating the proximal holes 43, the shaped scissors 9 having dimensions corresponding to those of the blade 10 of the blade suture clip 1.

It still remains to impact the blade suture clip 1, the blade 10 of which is introduced into the slit 45, while the teeth 11 are introduced into the distal holes 44.

While the blade suture clip 1 is in place, the positioning-reduction frame 2 and its means of attachment can be lifted.

The securance of the blade suture clip 1 can be increased by means of a screw introduced in a hole 14, represented by dotted lines in 1, pierced on the intermediate part 12 just below the teeth 11 of the clip 1.

It goes without saying that the present invention would not be limited to the preceding description and its methods of realization and it is susceptible to a number of modifications without leaving the scope of the invention.

The instrument of the present invention can notably be used for the installation of other implants used for reduction osteotomies, without requiring substantial modifications.

In the case of a blade-plate, for example, which differs from a blade suture clip only by the distal attachment being achieved by means of at least one screw instead of teeth, the piercing block contains holes allowing one to pierce holes designed to receive one or several screws in the bone.

What is claimed is:

1. Instrumentation for a blade suture clip for a reduction osteotomy for treatment of inflammation of the knee joint, the blade suture clip containing a proximal blade designed to be inserted in a slit pierced transversely in the epiphysis below the osteotomy and two distal teeth designed to be inserted in distal holes pierced under the osteotomy, the blade and the teeth being united by an intermediary presenting an indentation in order to create a focus such that the amplitude (A) is a function of the morphology of the tibia, the instrumentation comprising:

a piercing block for creating holes;

a positioning-reduction frame presenting an opening adapted for the positioning of the piercing block allowing the installation of the blade suture clip, the opening surrounded by two proximal edges, two distal edges and two lateral edges presenting an indentation corresponding to the shape of the blade-suture clip;

proximal and distal parts of the lateral edges of the positioning-reduction frame being substantially parallel but in different planes and spaced at a length corresponding to the amplitude (A) of an indentation of the blade suture clip;

the proximal part of each of the lateral edges containing superimposed holes adapted for the positioning of the positioning-reduction frame by means of pins;

the distal edge containing a hole designed for the passage of a proximal bit of a tightening instrument allowing an adjustment of a compression; and a distal bit introduced in a hole pierced in the tibia under the positioning-reduction frame at a distance from the distal edge 22 of the frame.

2. The instrumentation according to claim 1 wherein a first hole for the passage of the proximal bit of the tightening instrument is oblong in a vertical direction.

3. The instrumentation according to claim 1 wherein a second hole, situated above the first hole, receives a pin allowing the adjustment of the compression independent of the tightening instrument.

4. The Instrumentation according to claim 3 wherein the holes are pierced in an extension projecting towards the bottom of the distal edge of the positioning-reduction frame.

5. The instrumentation according to claim 1 further comprising: the piercing block containing at its proximal edge a series of holes juxtaposed and pierced in the frontal direction to allow the piercing of the holes into the bone for preparation of a slit in order to lodge the blade of the blade suture clip in the bone and, at its distal end, two side by side holes pierced in the frontal direction with the space between the two holes corresponding to the teeth of the blade suture clip.

6. The instrumentation according to claim 5 further comprising;
   the piercing block containing in its distal part a transverse hole allowing the adaptation of a maintenance handle to the piercing block.

7. The instrumentation according to claim 1 further comprising:
   a piercing template adaptable onto the positioning-reduction frame, the piercing template containing a distal extension which extends beyond the distal edge of the positioning-reduction frame and which is pierced in a frontal direction by a hole, allowing the piercing of the hole into the bone to introduce the distal bit of the tightening instrument.

8. The instrumentation according claim 7 wherein the piercing template further comprises:
   a proximal hook adapted to be introduced into the distal hole of the positioning-reduction frame and adapted for the passage of the proximal bit of a tightening instrument, the lower edge of the hole being indented into the side of the tibia.

9. The instrumentation according to claim 1, further comprising:
   the piercing block including a distal extension pierced in the frontal direction by a hole adapted to allow the piercing of the hole into the bone to introduce the distal bit of a tightening instrument.

10. An installation instrument for a blade-plate for a reduction osteotomy for the treatment of inflammation of the knee, the blade-plate containing a proximal blade adapted to be impacted in a slit pierced transversely in the epiphysis below the osteotomy, and at least one hole pierced in a distal part adapted to allow the attachment of the blade-plate by at least one screw, the proximal blade and the distal part being united by an intermediate portion presenting an indentation to create a gap having an amplitude which is a function of the morphology of the tibia, the instrumentation comprising:
   a positioning-reduction frame presenting an opening to the position of the piercing block in order to create holes allowing the installation of the blade-plate, the opening surrounded by two proximal edges, two distal edges two lateral edges presenting an indentation corresponding to the shape of the blade-plate;
   a proximal part of each of the lateral edges containing superimposed holes adapted for the positioning of the positioning-reduction frame by means of pins; and
   one distal edge containing a hole adapted for the passage of a proximal bit of a tightening instrument allowing an adjustment of the compression, the one distal edge adapted to be introduced in a hole pierced in the tibia under the positioning-reduction frame at a distance from the distal edge of the positioning-reduction frame.

* * * * *